United States Patent [19]

Eitner et al.

[11] Patent Number: 4,893,321
[45] Date of Patent: Jan. 9, 1990

[54] X-RADIATOR, PARTICULARLY FOR PRODUCING INTRA-ORAL DENTAL EXPOSURES

[75] Inventors: Dorothea Eitner, Erlangen; Hermann Kuehnke, Muenchaurach; Elisabeth Messingschlager, Wiesenttal; Dorothea Wilke, Erlangen, all of Fed. Rep. of Germany

[73] Assignee: Siemens Aktiengesellschaft, Berlin and Munich, Fed. Rep. of Germany

[21] Appl. No.: 121,180

[22] Filed: Nov. 16, 1987

[30] Foreign Application Priority Data

Nov. 21, 1986 [DE] Fed. Rep. of Germany ....... 3639773

[51] Int. Cl.⁴ .............................................. H01J 35/16
[52] U.S. Cl. ..................................... 378/121; 378/119; 378/193
[58] Field of Search ................... 378/121, 203, 38, 39, 378/193, 119

[56] References Cited

U.S. PATENT DOCUMENTS

| | | |
|---|---|---|
| 2,137,122 | 11/1938 | Humphreys . |
| 2,216,210 | 10/1940 | Mutscheller ........................ 378/203 |
| 3,812,366 | 5/1974 | Gralenski . |
| 4,157,476 | 6/1979 | O'Connor . |

OTHER PUBLICATIONS

Sales Brochure "Heliodent no" Siemens AG, Nr. Al 9100-M47-A306 West Germany WS 12838
Patent Abstracts of Japan, Vol 5 Number 82 (E-59) [754], May 29, 1981-for Japanese Published Application 56-30296 (A) Yoshio Mitsumura 3/26/81

FOREIGN PATENT DOCUMENTS

629610 5/1936 Fed. Rep. of Germany .
0030296 3/1981 Japan ................................. 378/121

Primary Examiner—Carolyn E. Fields
Assistant Examiner—David P. Porta
Attorney, Agent, or Firm—Hill, Van Santen, Steadman & Simpson

[57] ABSTRACT

An x-radiator, particularly useful for intra-oral dental exposures, includes a common housing having a barrel at one end, a high-voltage generator having a high-voltage transformer being arranged in the housing adjacent said barrel, and an x-ray tube being mounted in the housing at an end of the transformer opposite said barrel, said transformer having a cylindrical configuration having an opening with a longitudinal axis through which opening the x-ray beam passes from the x-ray tube through the transformer coil to the barrel.

15 Claims, 1 Drawing Sheet

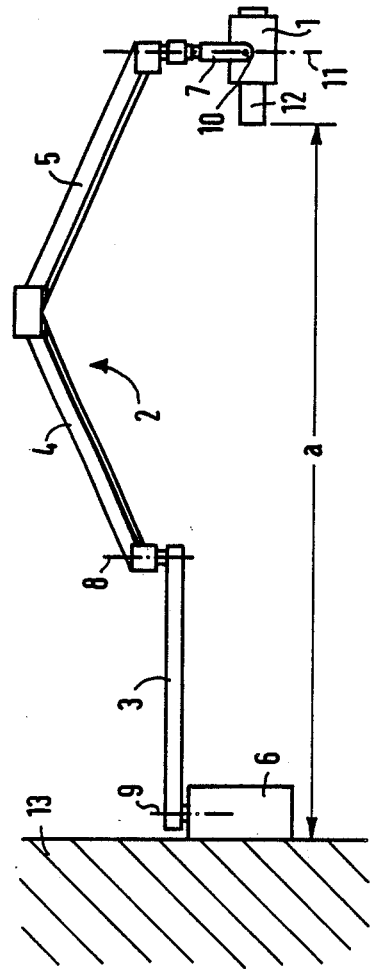
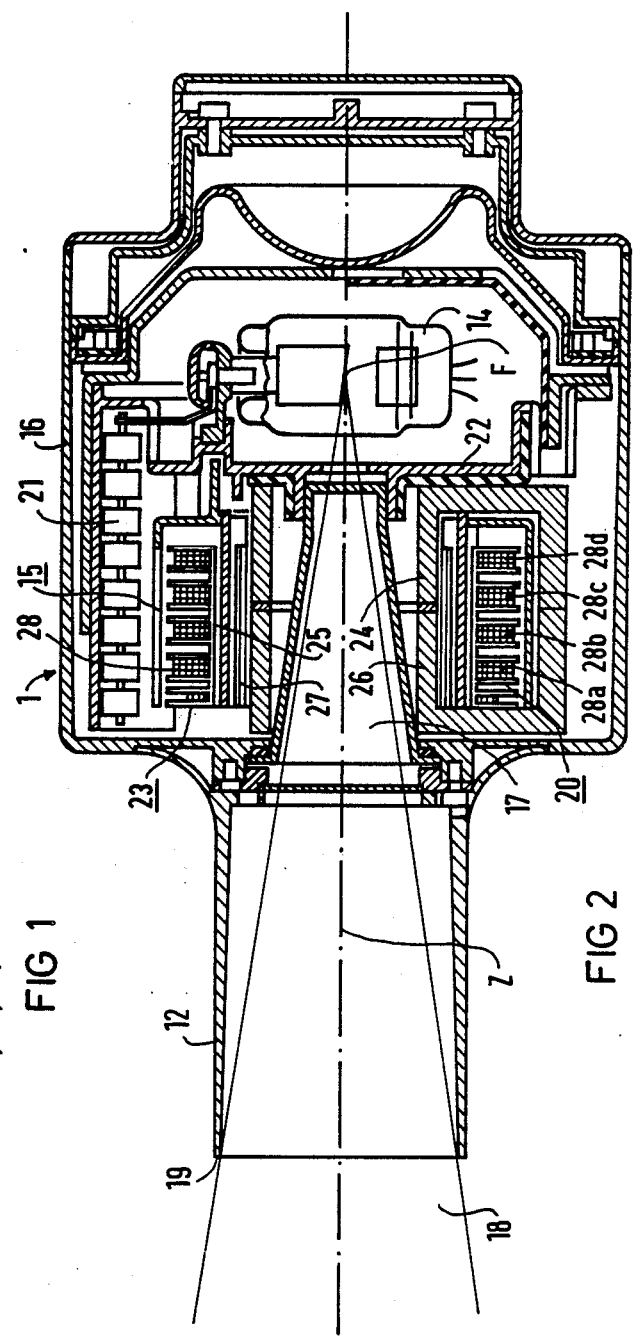

X-RADIATOR, PARTICULARLY FOR PRODUCING INTRA-ORAL DENTAL EXPOSURES

BACKGROUND OF THE INVENTION

The present invention is directed to an x-radiator, particularly for producing intra-oral dental exposures, which x-radiator has an x-ray tube and a high-voltage generator having a high-voltage transformer, which are arranged in a shared or common housing, to which a telescope barrel is connected. The high-voltage transformer is arranged between the x-ray tube and the telescope barrel and comprises a channel for the passage of the x-ray beam generated by the x-ray tube.

X-radiators for producing dental exposures, whose housings have a barrel which serves the purpose of assuring a certain minimum distance between the focus of the x-ray tube and the examination subject for reasons of radiation protection, are usually secured to a wall bracket. The bracket comprises a plurality of articulations, which allow the x-radiator to be aligned to the examination subject in an expedient way. In order to be able to undertake all required examinations, the wall bracket, as experience has shown, must exhibit such a length that it is possible to position the x-radiator horizontally aligned and directed at the wall such that an end face of the barrel has a distance of approximately 1.5 meters from that wall to which the wall bracket is secured. The wall bracket and the articulations thereof must absorb considerable stresses so that suitable measure must be undertaken in order to guarantee an adequate static stability of the wall bracket and in order to prevent vibrations of the wall bracket, which would diminish the exposure quality. Since an x-radiator is manually aligned to the examination subject, a handy housing shape is also desirable.

An x-radiator which is constructed so that the x-ray tube is arranged between the high-voltage transformer and the barrel, is disclosed in a sales publication or brochure entitled "Heliodent 70", Siemens AG, No. A19100-M47-A306. This x-radiator has a thin shape, which facilitates the manipulation; however, the center of gravity of the known x-ray tube is at a very great distance from the end face of the barrel. This has a disadvantageous effect on the stresses on the bracket, particularly given positions of the x-radiator in which it exhibits its greatest distance from the wall, and is aligned thereto. This stress is all the greater the farther the center of gravity of the x-radiator is distance from the end face of the barrel adjacent to the examination subject and, thus, from the wall.

An x-radiator, which has a tubular high-voltage transformer with a bore receiving an x-ray tube with the x-ray beam emerge through a channel of the high-voltage transformer, which channel extends transverse relative to the bore or axis of the transformer, is disclosed in German Pat. No. 629,610. In the case of this x-radiator, the high-voltage transformer is, thus, at least partially situated between the x-ray tube and the barrel so that a reduced distance of the center of gravity of the x-radiator from the end face of the barrel is present. This is an advantage in view of the stressing for the wall bracket. In order to achieve this advantage, however, the high-voltage transformer is constructed in a complicated and, consequently, costly fashion. In addition, the known x-radiator does not exhibit or provide a handy shape.

X-radiators of the species initially cited are also disclosed in U.S. Pat. Nos. 4,157,476, and 2,137,122. As a consequence of the arranging of the high-voltage transformer between the x-ray tube and the barrel, the center of gravity of these x-radiators is considerably closer to the end face of the barrel than in the case of the x-radiator, wherein the x-ray tube is arranged between the barrel and the high-voltage transformer. As a consequence of the channel provided in the high-voltage transformer, the latter exhibits a large outside dimension in the case of both of these known x-radiators, so that both x-radiators each have a bulky, roughly cuboid shape which runs counter to a comfortable manipulation.

SUMMARY OF THE INVENTION

The object of the present invention is to provide an x-radiator of the type initially described, wherein the center of gravity lies close to the end face of the barrel without causing the housing of the radiator to have an unhandy shape and without requiring a high-voltage transformer to have a complicated structure.

These objects are achieved in accordance with the present invention by an x-radiator, particularly for producing intra-oral dental exposures comprising a housing with a barrel connected thereto, an x-ray tube with an exit window, a high-voltage generator having a high-voltage transformer, said high-voltage transformer having a tubular winding with an inside wall forming an axially-extending opening, said high-voltage transformer being mounted in the housing adjacent the barrel with the axially-extending opening being aligned with the barrel, said x-ray tube being mounted at the other end of the high-voltage transformer with the exit window for the tube arrange so that an x-ray beam exiting the x-ray tube passes through the axial opening into the barrel.

Since the high-voltage transformer comprises a tubular or cylindrical winding with the inside wall forming an opening for the channel for the passage's x-ray beams, it becomes clear that the measure of the invention initially produces a favorable position of the center of gravity of the x-radiator, namely, close to the end face of the barrel. In addition, the high-voltage transformer can be manufactured in a simple way as a consequence of the tubular structure of its windings. Over and above this, it is possible to construct the housing for the x-radiator as a thin, handy and, in particular, rotational symmetrical shaped.

It is provided, in accordance with the modifications of the invention, that the high-voltage transformer comprises a tubular core arranged in the opening of the windings and that the channel for the passage of the x-ray beam proceeds through a bore of the core. As a consequence of this arrangement, the design of the core of the high-voltage transformer, it is assured that this assumes only a slight structural volume in a radial direction and, thus, does not oppose a handy design of the x-radiator.

The x-radiator of the invention can be provided with an especially handy shape when the high-voltage transformer is designed essentially rotational symmetric with reference to its longitudinal axis and when this corresponds to the central ray of the x-ray beam being emitted by the x-ray tube.

It is provided in accordance with one embodiment of the invention that the windings of the high-voltage transformer contain a primary winding and a secondary winding. The secondary winding is formed by a plurality of winding segments connected in series and arranged successively in the direction of the longitudinal axis of the high-voltage transformer and these winding segments surround the common, tubular fashion primary winding, which extend the axial length of all the winding segments. This measure, likewise, serves the purpose of a simple construction for the high-voltage transformer and, as a consequence of the division of the secondary windings into the individual winding segments assures a high electrical strength of the secondary windings.

As a consequence of the described formation of the high-voltage transformer, it is possible to arrange component parts of the high-voltage generator on the periphery of the high-voltage transformer, in a space-saving fashion.

Another embodiment of the invention provides that the x-ray tube and high-voltage generator form a structural unit. This measure makes it possible to already adjust the position of the x-ray tube relative to the high-voltage generator or, respectively, to the channel provided in the high-voltage transformer thereof outside of the housing and to mount both in common in a housing in one assembly step.

Other advantages and features will be readily apparent from the following description of the preferred embodiment, the drawings and claims.

BRIEF DESCRIPTION OF THE DRAWINGS

FIG. 1 is a side view of the x-radiator of the present invention attached to a wall bracket; and FIG. 2 is a longitudal cross sectional view of an x-radiator of the invention.

DESCRIPTION OF THE PREFERRED EMBODIMENTS

The principles of the present invention are particularly useful when incorporated in an x-ray generator 1, which is attached to a wall bracket 2. The wall bracket 2 is composed of bracket sections 3, 4 and 5, as well as a wall mount 6, and a mount 7 for the x-radiator 1.

The mount 7 is connected to the bracket section 5, and this bracket section is connected with a hinge-type joint to a bracket section 4. The bracket section 4 is connected by an articulated joint to a bracket section 3 so that it can be pivoted around an axis extending perpendicular to the plane of the drawing. In addition, the bracket section 4 is also pivotable around an axis 8 relative to the bracket section 3. The bracket section 3 is connected by a pivotable joint to a wall mount 6 so that it can pivot around a vertical axis 9. The wall mount 6, as illustrated, is attached to a wall 13. The x-radiator 1 is arranged on a mount 7, which allows pivoting around both axes 10 and 11, wiich axes extend at right angles to each other.

The x-radiator 1 can, thus, be arbitrarily positioned within certain limits, which are established by the dimensions of the bracket sections 3, 4 and 5 and by the range of pivots of the articulated joints. As illustrated in FIG. 1, the x-radiator 1 is positioned with the end face of a barrel 12 that is attached to the radiator 1, exhibiting the greatest possible distance a from the wall 13.

As best illustrated in FIG. 2, the x-radiator 1 includes an x-ray tube 14 and a high-voltage generator 15, which are arranged in a common housing 16. The housing 16, at one end, has the barrel 12 connected thereto.

The high-voltage generator 15 comprises a high-voltage transformer 20, which is arranged between the x-ray tube 14 and the barrel 12. This high-voltage transformer 20 comprises a channel 17, through which an x-ray beam 18 emitted from a window of the x-ray tube 14 proceeds. As a consequence of the structure, and given the prescribed distance between an end face 19 of the barrel 12 and a focus F of the x-ray tube 14, it becomes clear, without further ado, that the x-radiator 1 of the invention comprises a considerably shorter structural length than the x-radiator, wherein the x-ray tube is arranged between the barrel and the high-voltage transformer. With reference to FIG. 1, it also becomes clear that the x-radiator of the invention represents only a slight stress for the wall bracket 2, given a permanently prescribed distance a between the wall 13 and the end face 19 of the tube 12, since the center of gravity of the x-radiator 1 of the invention lies close to the end face 19 of the barrel and, thus, closer to the wall 13.

As FIG. 2 also illustrates, the high-voltage transformer 20 comprises a tubular winding 23. As a consequence of a tubular shape, the inside wall of the winding 23 defines an opening 25, which extends along the axis of the winding and through the entire winding 23. An essential tubular core 24 is arranged in the opening 25 of the winding 23. As best seen in FIG. 2, the channel 17, thus, proceeds through the opening 25 of the winding 23 by extending through a bore 26 of the core 24, which is arranged in the opening 25.

The winding 23 of the high-voltage transformer 20 contains a primary winding 27 and a secondary winding 28. The secondary winding 28 is formed by a plurality of winding segments 28a, 28b, 28c and 28d which are connected in series and arranged successively in the direction of the longitudinal axis of the high-voltage transformer. These winding segments 28a–28d surround the tubularly or cylindrically constructed primary winding 27, which is shared by all the winding segments 28a–28d. The high-voltage transformer is constructed in an essentially rotational-symmetrical fashion, and is arranged so that its longitudinal axis corresponds to the central ray Z of the x-ray beam 18. As a consequence of the described construction of the high-voltage transformer 20 and of its arrangement relative to the x-ray tube 14, it is possible to construct the housing 16 of the x-radiator as a thin, rotationally symmetrical shape, which is a handy shape.

The remaining component parts of the high-voltage generator 15, for example capacitors 21, which serve the purpose for voltage multiplication, are arranged at the periphery of the high-voltage transformer 20. The x-ray tube 14 and the high-voltage generator 15 are joined with a cap part 22 to form a structural unit, which can be assembled into the housing 16 in a simple manner.

Although various minor modifications may be suggested by those versed in the art, it should be understood that we wish to embody within the scope of the patent granted hereon all such modifications as reasonably and properly come within the scope of our contribution to the art.

We claim:

1. An x-radiator, for producing intra-oral dental exposures, said x-radiator comprising a common housing having a barrel with a first axis at one end of the housing, an x-ray tube having a window for emitting x-ray beams on a beam path, a high-voltage generator having a high-voltage transformer, said high-voltage transformer comprising a tubular winding extending on a longitudinal axis of symmetry with an inside wall forming an axial opening extending on said longitudinal axis, said transformer being positioned in the housing adjacent the barrel with the axial opening being parallel to the first axis of the barrel, said x-ray tube being positioned at an end of the transformer opposite the barrel with the window arranged so that the x-ray path extends along the longitudinal axis and through the axial opening to the barrel of the housing.

2. An x-radiator according to claim 1, wherein the high-voltage transformer includes a tubular core arranged in the axial opening of the winding, said tubular core forming the passage for the x-ray beam path proceeding from the x-ray window of the tube to the barrel.

3. An x-radiator according to claim 2, wherein the high-voltage transformer is constructed in an essentially rotational-symmetrical fashion relative to the longitudinal axis of the tubular winding, said axis corresponding to the path of the x-ray beam.

4. An x-radiator according to claim 3, wherein the tubular windings of the high-voltage transformer contain a primary winding with a tubular construction and a secondary winding, said secondary winding being formed as a plurality of winding segments connected in series and arranged successively in an axial direction of the longitudinal axis of the opening in the high-voltage transformer, said winding segments surrounding the tubular-constructed primary windings, which extend for the full length of the winding segments of the secondary winding.

5. An x-radiator according to claim 4, wherein component parts of the high-voltage generator are arranged on a periphery of the high-voltage transformer.

6. An x-radiator according to claim 5, wherein the x-ray tube and the high-voltage generator are formed as a structural unit within said housing.

7. An x-radiator according to claim 1, wherein the high-voltage transformer is constructed in an essentially rotational-symmetrical fashion relative to the axis of the opening.

8. An x-radiator according to claim 7, wherein the windings of the high-voltage transformer contain a cylindrical primary winding and a secondary winding, said secondary winding being formed by a plurality of winding segments connected in series and arranged successively in the direction of the axial opening of the high-voltage transformer, said winding segments surrounding the cylindrical, primary winding, which is shared by all of said winding segments.

9. An x-radiator according to claim 8, wherein component parts of the high-voltage generator are arranged along an outer periphery of the high-voltage transformer.

10. An x-radiator according to claim 9, wherein the x-ray tube and the high-voltage generator are connected by a structural member to form a single structural unit.

11. An x-radiator according to claim 1, wherein the x-ray tube is mounted on a portion of the high-voltage generator to form a single structural unit for assembly within said housing.

12. An x-radiator according to claim 1, wherein the windings of the high-voltage generator contain a primary winding having a cylindrical configuration and a secondary winding, said secondary winding being formed by a plurality of winding segments, which are connected in series and arranged successively in the direction of the axis of the high-voltage transformer, said winding segments surrounding the cylindrical primary winding, which extends the length of the winding segments.

13. An x-radiator according to claim 12, wherein component parts of the high-voltage generator are arranged on the periphery of the high-voltage transformer.

14. An x-ray generator for producing intra-oral dental exposures, said x-ray generator comprises a cylindrical housing having a cylindrical axis and a barrel disposed at one end on said cylindrical axis, an x-ray tube having a window for emitting x-rays along a beam path, a high-voltage generator having a high-voltage transformer, said high-voltage transformer including a tubular core having a longitudinal axis of symmetry and windings being provided on said core, said high-voltage generator being mounted in the housing adjacent the one end of the housing with the longitudinal axis of the tubular core being aligned with the barrel and extending parallel to the cylindrical axis of the housing, and said x-ray tube being mounted on an opposite end of the high-voltage generator with the window emitting the beam on said longitudinal axis to extend through said core and barrel.

15. An x-ray generator according to claim 14, wherein the high-voltage transformer contains a primary winding having a cylindrical configuration on said core, and a secondary winding, said secondary winding being formed by a plurality of winding segments connected in series and being arranged successively in the direction of the longitudinal axis of said core, said winding segments surrounding the primary winding, which extends the length of all of said winding segments.

* * * * *